US006855147B2

(12) United States Patent
Harrington, Jr.

(10) Patent No.: US 6,855,147 B2
(45) Date of Patent: Feb. 15, 2005

(54) MODULAR ANTERIOR CERVICAL PLATE

(75) Inventor: James Frederick Harrington, Jr., 24 Keene St., Providence, RI (US) 02905

(73) Assignee: James Frederick Harrington, Jr., Providence, RI (US)

( * ) Notice: Subject to any disclaimer, the term of this patent is extended or adjusted under 35 U.S.C. 154(b) by 52 days.

(21) Appl. No.: 10/136,076

(22) Filed: Apr. 29, 2002

(65) Prior Publication Data

US 2003/0023242 A1 Jan. 30, 2003

Related U.S. Application Data

(63) Continuation-in-part of application No. 09/560,415, filed on Apr. 27, 2000, now abandoned.
(60) Provisional application No. 60/131,629, filed on Apr. 28, 1999.

(51) Int. Cl.[7] ............................................. A61B 17/58
(52) U.S. Cl. ....................................................... 606/69
(58) Field of Search ........................ 606/60, 61, 69–71, 606/105; 623/17.11

(56) References Cited

U.S. PATENT DOCUMENTS

| | | | |
|---|---|---|---|
| 3,242,922 A | 3/1966 | Thomas | |
| 4,382,438 A | 5/1983 | Jacobs | |
| 4,657,550 A | 4/1987 | Daher | |
| 4,714,469 A | 12/1987 | Kenna | |
| 5,108,394 A | 4/1992 | Kurokawa | |
| 5,108,395 A | 4/1992 | Laurain | |
| 5,344,421 A | 9/1994 | Crook | |
| 5,439,463 A | 8/1995 | Lin | |
| 5,470,333 A | 11/1995 | Ray | |
| 5,487,743 A | 1/1996 | Laurain et al. | |
| 5,545,166 A | 8/1996 | Howland | |
| 5,578,127 A | 11/1996 | Kimura | |
| 5,616,142 A | 4/1997 | Yuan et al. | |
| 5,693,053 A | 12/1997 | Estes | |
| 5,707,372 A | * 1/1998 | Errico et al. | ................... 606/61 |
| 5,728,127 A | 3/1998 | Asher et al. | |
| 6,159,213 A | 12/2000 | Rogozinski | |
| 6,340,362 B1 | * 1/2002 | Pierer et al. | ................... 606/71 |

FOREIGN PATENT DOCUMENTS

| | | |
|---|---|---|
| DE | DE 4438264 A1 | 3/1996 |
| EP | EP 455255 | 6/1991 |

OTHER PUBLICATIONS

"ABC, Anterior Cervical Plating System," Surgical technique, as described by Apfelbaum, R.I. (brochure) 1999, Aesculap, 1000 Gateway Boulevard, South San Fransisco CA 94080.

"Atlantis, Anterior Cervical Plating System," Surgical technique, as described by Sonntag, V.K.H. et al., (brochure) 1998, Sofamor Danek USA 1800 Pyramid Place, memphis, TN 38132.

"Orion, Anterior Cervical Plating System," Surgical technique, as described by Lowery, G.L. (brochure) 1998, Sofamor Danek USA 1800 Pyramid Place, Memphis, TN 38132.

* cited by examiner

Primary Examiner—Kevin Shaver
Assistant Examiner—Michael B. Priddy
(74) Attorney, Agent, or Firm—Lowrie, Lando & Anastasi, LLP

(57) ABSTRACT

An anterior cervical plate system consists of a base plate and a connecting plate movably connected to the base plate. The base plate can be inserted into any number of cervical vertebral bodies in any one construct. The base plate contains holes for two unicortical bone screws and a third hole to accommodate a rather large diameter, but short screw that movably secures the connecting plate, and raised middle portion to strengthen screw purchase and fit of the connecting plate. The connecting plate has a central trough opening to accommodate this screw.

46 Claims, 6 Drawing Sheets

MODULAR ANTERIOR CERVICAL PLATE

RELATED APPLICATION

This application is a Continuation-in-Part of U.S. patent application Ser. No. 09/560,415, filed Apr. 27, 2000 abandoned, which claims the benefit of U.S. Provisional Patent Application Ser. No. 60/131,629 filed on Apr. 28, 1999, the contents of which are herein incorporated by reference.

BACKGROUND OF THE INVENTION

This invention relates to a modular anterior cervical plate designed to provide internal stabilization (temporary strengthening) to the spine in the cervical region (neck) during surgical repairs through an anterior approach to the neck.

This device is designed to improve healing and make it more likely that surgical fusion will be followed by bony union, and reduce the need for external braces following surgery. This is not the first anterior cervical plate ever designed, but it has several novel features that will facilitate decompressive aspects of cervical spine surgery, and will facilitate compression and distraction during cervical fusion and will allow dynamic settling if necessary in the first several weeks after surgery.

Devices presently on the market are basically thin (less than about 2.5 mm thick) molded metal plates that bridge gaps in the front of the cervical spine caused by surgery. (Examples are the Orion plate by Sofomor-Danke, the Codman plate by Johnson and Johnson, the Morsher plate by Synthes Inc., the Acromed plate, and others.) They stabilize the spine when screws are inserted through holes in the plate into bone above and below the surgical gap in the spine. As such, all plates on the market today are basically a single unit design.

SUMMARY OF THE INVENTION

The present invention provides an anterior cervical plate comprising modular parts: a pair of base plates and a connecting plate. The connecting plate is connected to the base plates so as to allow a controlled movement between the base plates and the connecting plate. The base plate design has two advantages. First, because of its small size, it does not obscure surface landmarks on the spine, reducing instances of errant screw insertion and surgical complications. When surface landmarks are obscured, chances for errant screw insertion and surgical complications increase. Secondly, the base plate can be used with distracting instruments to facilitate distraction during dicectomy or other decompressions, which is not a feature of any other anterior plate design. Distracting instruments, such as distracting forceps, stretch the vertebrae of the spine by bearing against distraction-compression portions on the base plates. The base plate may also be designed to interface with retractor blades.

The anterior cervical plate of the invention facilitates decompressive aspects of cervical spine surgery, and facilitates distraction (i.e. stretching of the spine) during cervical fusion. The base plate and connecting plate combination allows for insertion of fusion bone with distraction or compression, finely manipulated by the surgeon. No other plate design allows for this. With all other plates, one must rely on the tightness of fit obtained with the fusion bone (the degree to which the bone achieves a proper fit) to maximize conditions for fusion. The tighter the fit, the more likely fusion is to take place. Since this plate can maximize compression forces beyond what can be obtained with traditional plate designs, fusion rates should be higher. Finally, the connecting plate to base plate interface can be modified to allow dynamic settling of the spine over several weeks time in the saggital and coronal planes to the spine. Particularly when large surgical gaps are created, this kind of settling caused by gravity is felt to promote and enhance fusion. This function is available in only one other plate design on the market (Acromed), but by a different mechanism.

These advantages are derived from the modular design. With the development of a thickened midsection of the base plate, a lock screw has been shown in pullout tests to hold the two plates together very tightly, while allowing a controlled movement at the interface. While a controlled movement at the interface between the connecting plate and the base plate is allowed, the connecting plate is constrained from rotational movement by raised distraction and compression knobs at the lateral margins of the base plate. Therefore, the design will not fail under expected mechanical stresses, yet the unique advantages of the modular design will remain.

DETAILED DESCRIPTION OF THE INVENTION

The present invention provides an anterior cervical plate designed to facilitate settling of the spine in the saggital and coronal planes by allowing a controlled movement between a base plate assembly and a connecting plate. The invention will be described below relative to an illustrative embodiment. One skilled in the art will recognize that the invention is not limited to the illustrative embodiment and that variations may be made in accordance with the teachings and scope of the invention.

The anterior cervical plate of an illustrative embodiment of the present invention includes a pair of base plates for engaging vertebral bodies and a connecting plate connecting the two base plates. The anterior cervical plate is used to stabilize the spine during spinal surgery by aligning and maintaining the vertebral bodies in selected positions and orientations relative to each other to promote and enhance spinal fusion of the vertebral bodies.

Figure 1:
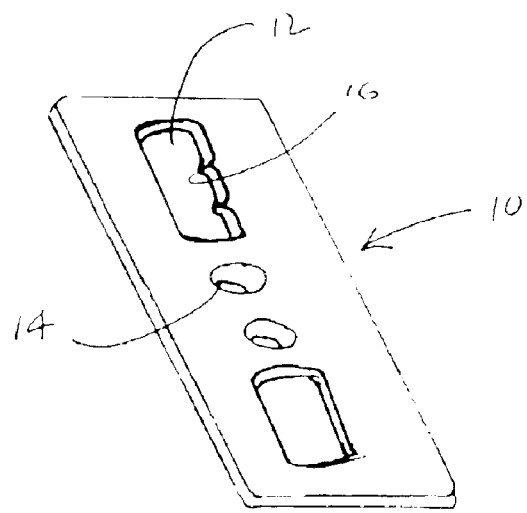
FIG. 1 is a perspective view of the connecting plate of the invention.

As shown in FIG. 1, the connecting plate 10 of the invention is a generally rectangular plate, preferably made from an alloy having good corrosion resistance, relatively low density and high strength and durability, such as titanium or a titanium alloy. One skilled in the art will recognize that any suitable materials may be used to form the plate. The connecting plate has screw slots 12 at either end, and at least two screw holes 14 in the middle for receiving bone graft screws or another suitable fastening element for connecting the connecting plate to a bone graft. One skilled in the art will recognize that the invention is not limited to bone graft screws and that any suitable fastening element, such as a pin, can be used.

In a preferred embodiment, the connecting plate is between about 1.9 mm and about 3.1 mm thick. Preferably, the connecting plate is about 2.02 mm thick. The length of the connecting plate may vary, for example, at 5 mm intervals, from about 20 mm to about 110 mm. The width of the illustrative connecting plate may be between about 15 mm and about 18 mm and is preferably about 16 mm.

Figure 2:
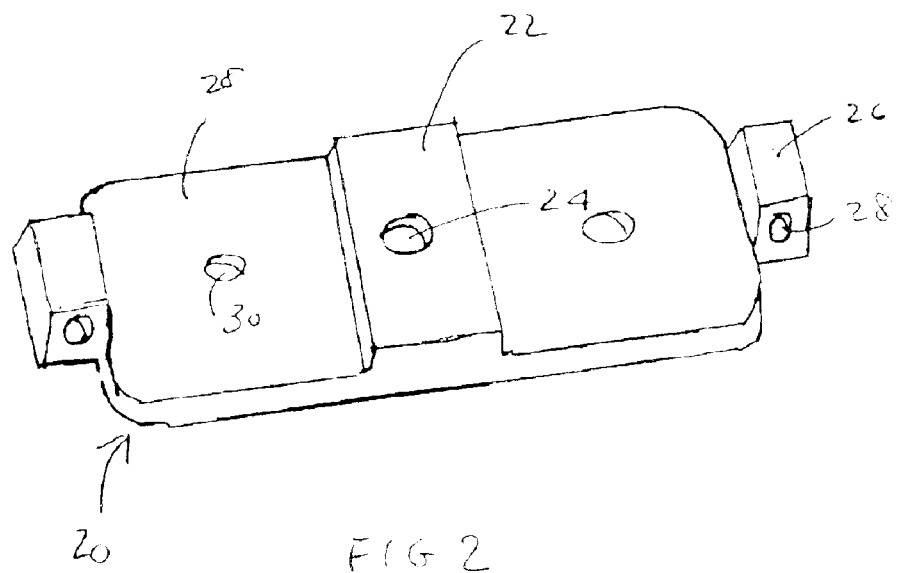
FIG. 2 is a perspective view of the base plate of the invention.

The base plate 20, as shown in FIG. 2, is generally rectangular, and preferably has a width of between about 8 mm and about 10 mm and preferably about 9 mm, a length of between about 18 mm and about 22 mm and preferably about 20 mm, and a maximum height, i.e. a raised central section 22, of between about 1.5 mm and about 3 mm and preferably about 2.54 mm. One skilled in the art will recognize that the base plate is not limited to the illustrative dimensions and that variations in the width, length and thickness may be made. The base plate 20 may also be formed of titanium or a titanium alloy, though one skilled in the art will recognize that any suitable material may be used.

Figure 3:
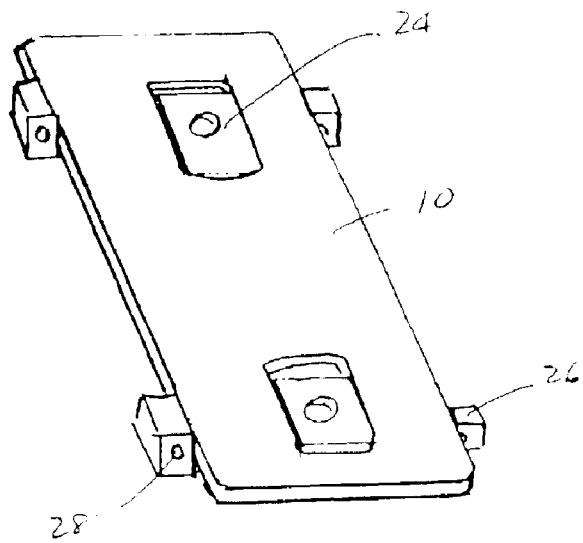
FIG. 3 is a perspective view of the connecting plate and two base plates, as they would be assembled in use.

Each base plate 20 includes a raised central section 22 that is generally rectangular and insertable in one of the screw slots 12 of the connecting plate 10 (see FIG. 3). The base plate raised central section 22 has a threaded screw hole 24 for receiving a central screw 25, preferably of titanium alloy, for securing the base plate 20 to the connecting plate 10. One skilled in the art will recognize that other suitable materials may be used to form the screw 25. The illustrative screw 25 has a 6/32 thread with 3 turns over about 2.0 mm, though the invention is not limited to these parameters. The threaded screw hole 24 may or may not extend through the base plate 10. The screw slot 12 and the central screw 25 may form a controllably movable interface between the base plate 20 and the central plate 10, to be described in detail below.

At either side of the base plate 20 are raised distraction-compression knobs or portions 26, defining holes 28 oriented parallel to the spine, for the insertion of elements of distraction tools.

Between the raised central portion 22 of the base plate and the distraction-compression sections 26 at either end, are planar reduced thickness sections 28 (between about 0.25 mm and about 1 mm thick and preferably about 0.5 mm thick). These reduced thickness sections 28 of the base plate include two or more bone screw holes 30 for receiving unicortical bone screws, to attach the base plate to vertebral bodies. According to an illustrative embodiment, the bone screws 32 have an outside diameter of between about 3 mm and about 4.5 mm and preferably about 3.5 mm and a length between about 14 mm and about 18 mm.

Figure 4:
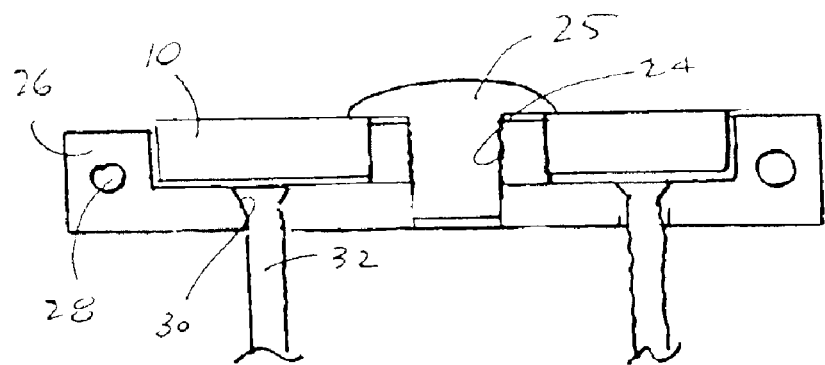
FIG. 4 is a cross sectional view of the assembled device according to one embodiment.
Figure 5:
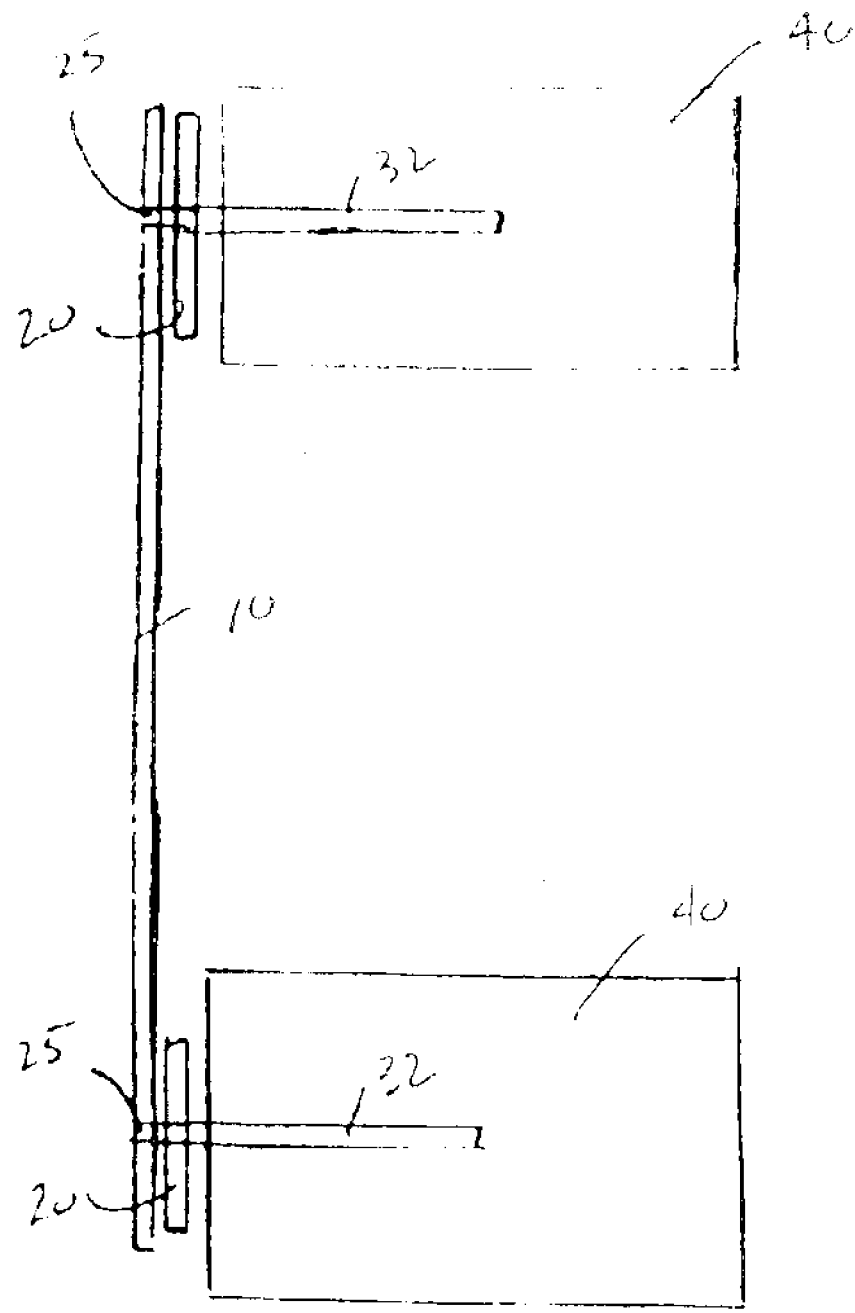
FIG. 5 is a schematic side view of the assembly of the invention attached to the spine.

To stabilize the spine using the anterior cervical plate of the present invention, retractor blades may be utilized to initially expose and provide access to the anterior vertebral column. As shown in FIG. 4 and FIG. 5, a pair of base plates 20 are secured to vertebral bodies 40 in the spine by bone screws 32 passing through the bone screw holes 30 of the base plate 20. The connecting plate 10 is placed over the base plates 20 (see FIG. 3), and the central screw 25 is threaded into each base plate screw hole 24 to secure the connecting plate 10 to the base plates 20. The width of the base plate central section 24, and the distance between the base plate central section 24 and the distraction-compression knobs 26 are selected so that the connecting plate 10 fits snugly and angular movement of the connecting plate 10 relative to the base plate 20 is prevented.

Figure 6:
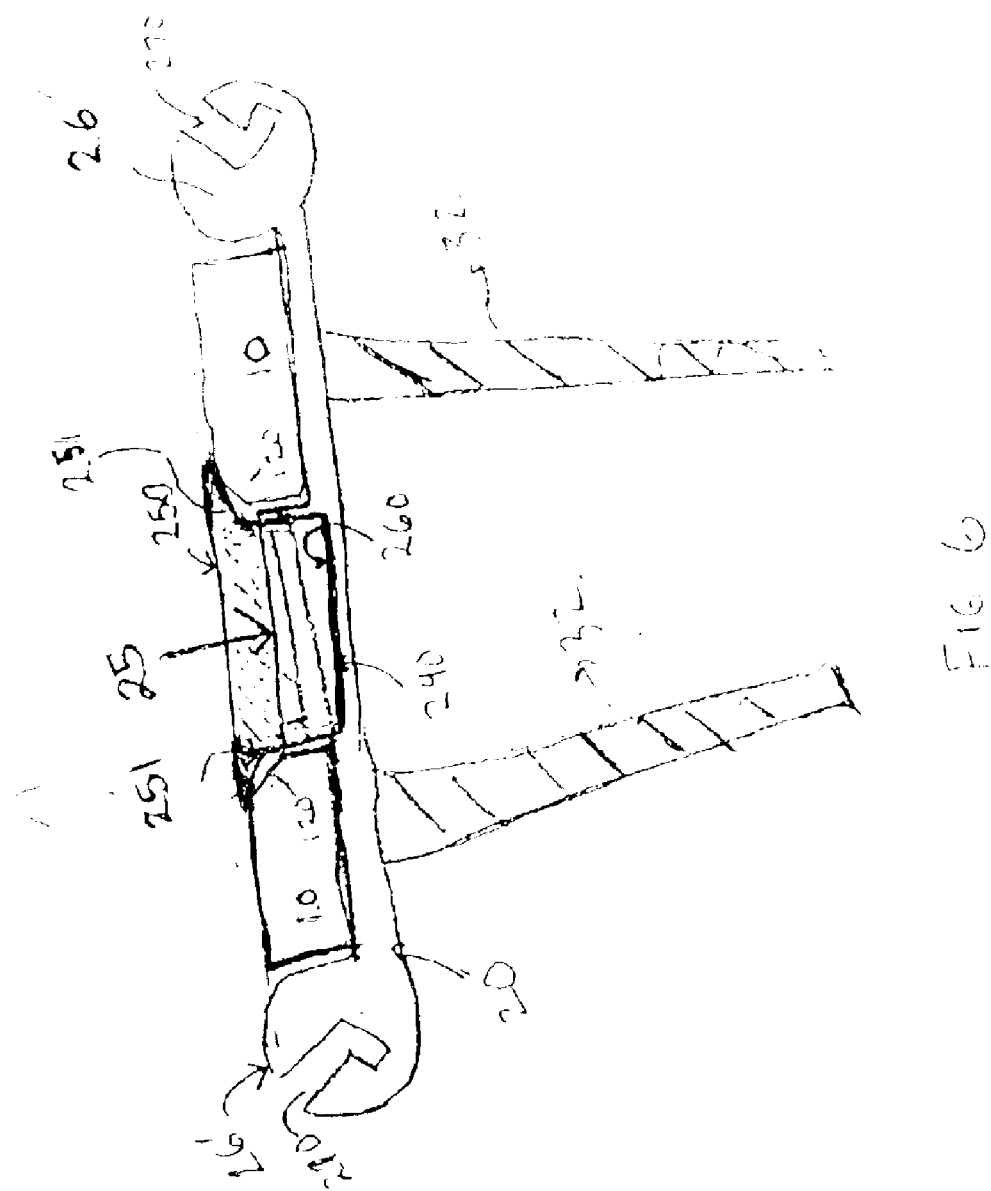
FIG. 6 is a cross sectional view of the assembled device according to another embodiment, using lock screws to provide a movable interface between the base plates and the connecting plate.

According to one embodiment, shown in FIG. 6, the central screw 25 may comprise a lock screw to allow for a controlled movement between the base plates 20 and the connecting plate 10 during fusion of the spine. As shown, the perimeter of the screw slot 12 of the connecting plate 10 may comprise a beveled edge 120 that contacts the edge 251 of the screw head 250 to connect the base plate 20 to the connecting plate 10. The amount of surface area contact between the beveled edge 120 of the slot 12 and the edge 251 of the screw head 250 determines the amount of friction holding the connecting plate to the base plate and may be varied to allow for controlled movement between the base plate and the connecting plate. For example, the length and configuration of the screw 25 and the angle of the edge 251 of the screw head 250 may be varied to provide varying amounts of pressure between the screw and the connecting plate. As shown in FIG. 6, the screw 25 may be configured to allow minimal surface area contact with the connecting plate 10, resulting in less friction at the base plate to connecting plate interface, thereby allowing the base plate 20 to controllably slide in the slot 12 relative to the connecting plate 10. Alternatively, the beveled edge 120 may slope at substantially the same angle as the edge 251 of the screw head 250 to increase the amount of contact between the edge 251 of the screw and the beveled edge 120 of the slot, thereby providing a relatively tighter fit.

Over the course of healing and fusion of the vertebrae, different screws 25 may be inserted to vary the amount of contact between the connecting plate edge and the screw, which varies the amount of force holding the base plate to the connecting plate and allows a controlled movement of the base plate along the slot of the connecting plate.

According to another embodiment, the movable interface may be achieved by increasing the length of the body of the lock screw, i.e. the threaded portion, such that the threaded portion is longer than the length of the screw hole 24. The increased length of the screw 25 relative to the screw hole 24 causes the screw head 250 to protrude from the screw hole 24 and the connector plate slot 12. When the lock screw 25 is screwed into the threaded hole 24 of the base plate 20, the bottom surface 260 of the screw 25 abuts the bottom surface 240 of the threaded hole 24. When the bottom surface 260 abuts the bottom surface of the threaded hole 24, the screw head 250 sits slightly above, and spaced from, the beveled edge 120 of the connecting plate 10. The screw head thus forms a gap between the edge 251 of the screw head 250 and the beveled edge 120 on the connecting plate 10. The gap between the screw head 250 and the connecting plate 10 may allow for a controlled movement of the connecting plate 10 relative to the base plate 20. The lock screw 25 limits the amount of relative movement between the connecting plate 10 and the base plate 20.

According to an alternate embodiment, the screw head 250 may have a flat edge, rather than a beveled edge, and/or the perimeter of the slot 12 may also be flat. The contact area between the edge of the screw head and the perimeter of the slot may be varied, allowing for a controlled movement of the connecting plate relative to the base plate. One skilled in the art will recognize that any suitable configuration for varying the amount of surface contact area between the screw head and the connecting plate or for forming a gap between the screw head and the slot may be utilized to allow for a controlled movement between the base plate and the connecting plate.

The length of the threaded hole 24 and the screw 25 and the configuration of the screw head 250 may be specifically selected to determine the contact area and control the amount of potential movement between the connecting plate and the base plate when anterior cervical plate is assembled. One skilled in the art will recognize that alternate means for providing a movable interface may be utilized according to the teachings of the invention.

The ability to provide a controlled movement between the base plate and the connecting plate allows for compression or distraction of the spine during the performance of a decompression and facilitates decompression or compression during subsequent fusion of the vertebrae. This controlled movement of the base plate and the connecting plate relative to each other allows gravitational settling to place further compression on a graft as the base plate moves along the slots in the connecting plate. The controlled movement thus promotes, facilitates and enhances a controlled amount of settling of the vertebrae, while preventing rotation, falling and flexing of the connecting plate, which significantly improves healing and fusion of the vertebrae in the cervical region of the spine.

As also shown in FIG. 6, the distraction-compression knobs 26' may be configured to interface with retractor blades. The distraction-compression knobs 26' include slots 270 configured for the insertion of retractor blades. The details of the retractor blade interface will be described in detail below.

Figure 7:
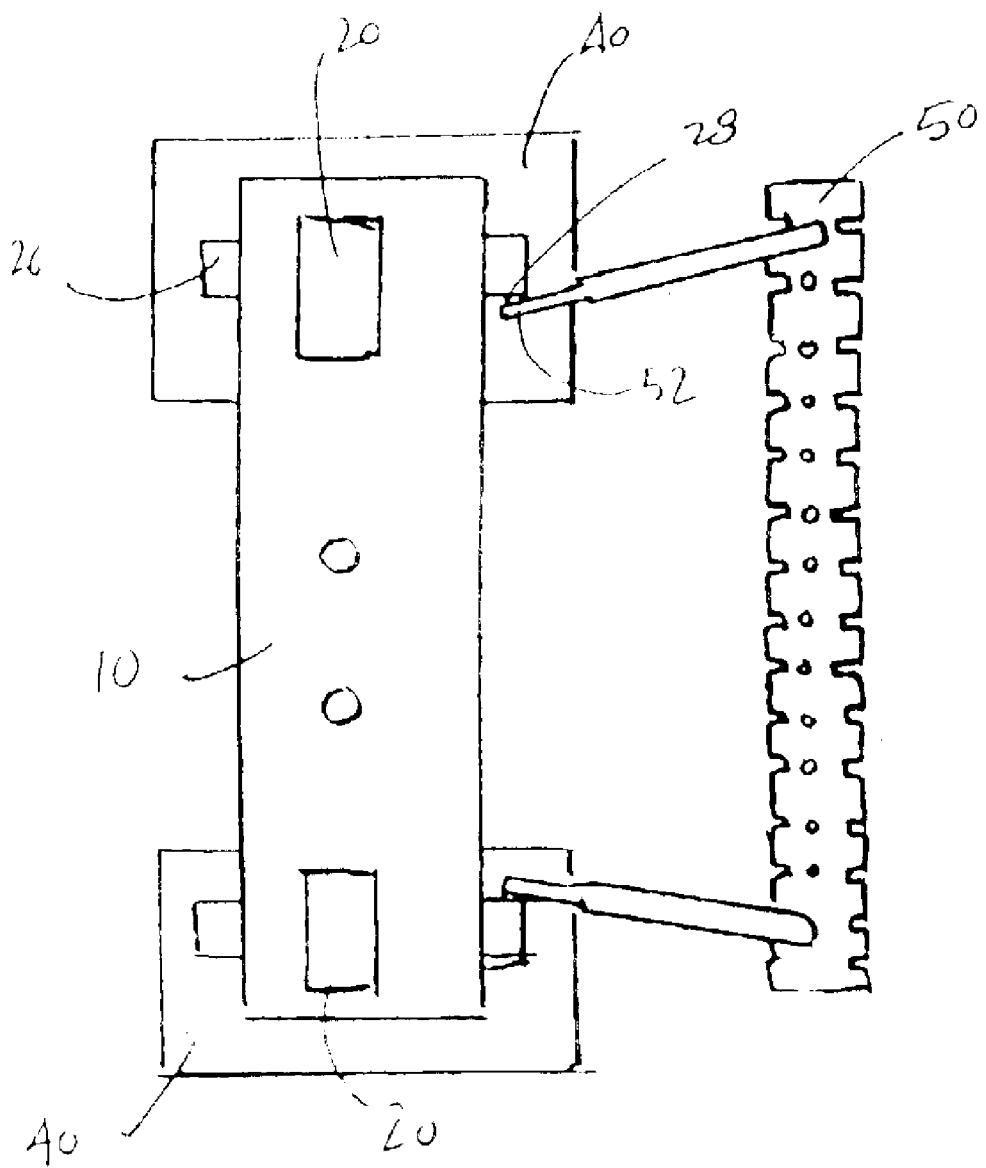
FIG. 7 is a schematic plan view of the assembly of the invention attached to the spine, with a distraction tool attached.

As shown in FIG. 7 a distraction tool 50 may be used with the assembly 10. Pins 52 the distraction tool 50 are insertable into the holes 28 the distraction-compression knobs 26. The assembly facilitates distraction by allowing for a controlled movement between the connecting plate and the base plates when a force is applied to the distraction-compression knobs 25 by the pins 52 of the distraction tool. In this manner, fusion of the spine is promoted, enhanced and accelerated.

Figure 8:
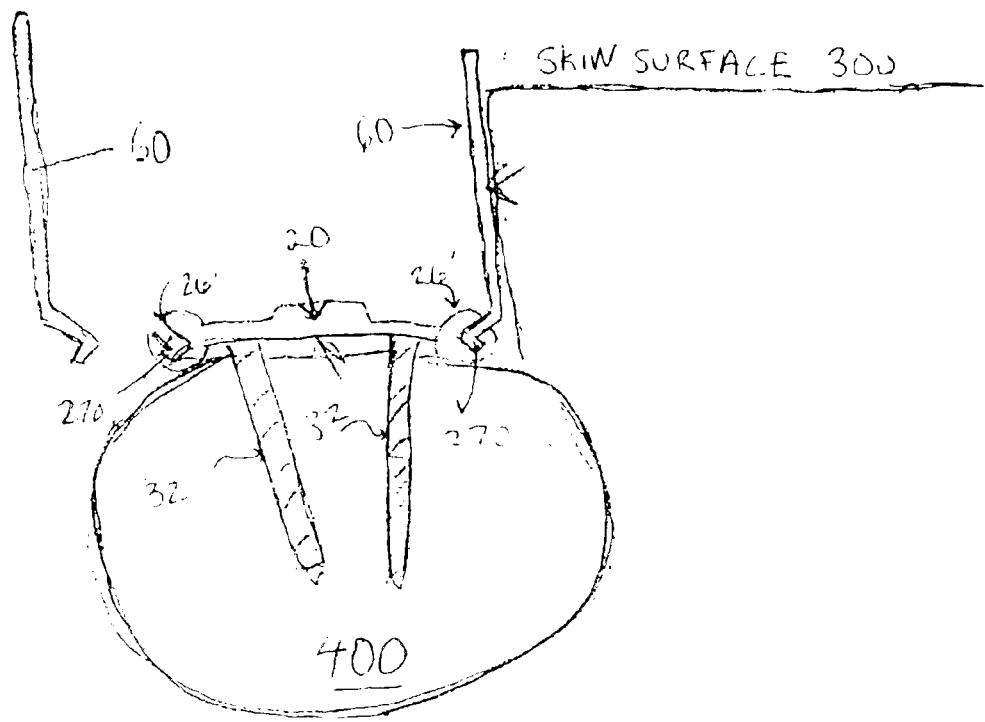
FIG. 8 is a cross sectional view of the assembled device attached to the spine according to an embodiment of the invention, with a retractor blade attached.
Figure 9:
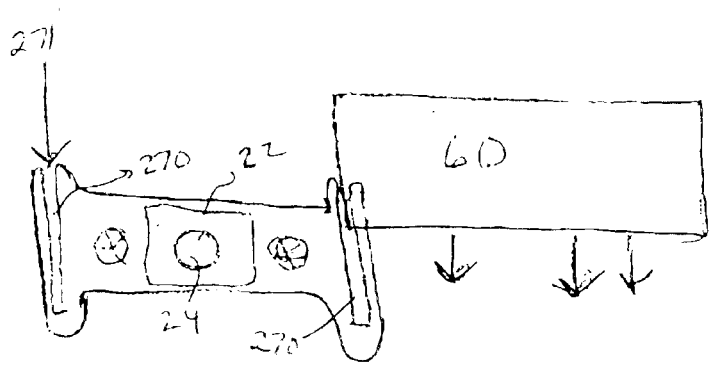
FIG. 9 is a top view of a base plate, illustrating the process of inserting a retractor blade into a retractor knob of the base plate.

As shown in FIG. 8 and FIG. 9, retractor blades may also be used with the assembly 10. The retractor blades are used to hold open an incision in the skin 300 to expose and provide access to the spine 400. As shown in FIG. 8, the retractor blades 60 are unattached to the base plate 20 and may be inserted into the slots 270 on knobs 26' of the base plate 20. As shown in FIG. 9, the retractor blade fits into an open end 271 of the slot 270, which is formed at a first end of the knob 26' in the base plate 20 and slides through the slot 270 to allow for retraction. The slot 270 may includes a closed end 272 to retain the retraction blade 60.

Variations on the assembly are possible. For example, the connecting plate 10 may have screw notches in one or both of the screw slots 12.

A preferred material to construct the modular anterior cervical plate assembly of the present invention is titanium, though one skilled in the art will recognize that alternate materials may be utilized.

Since certain changes may be made in the above constructions without departing from the scope of the invention, it is intended that all matter contained in the above description or shown in the accompanying drawings be interpreted as illustrative and not in a limiting sense. It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

1. A modular anterior cervical plate assembly comprising:
 a first base plate comprising means for attachment to a first vertebral body and a connecting plate fastener hole;
 a second base plate comprising means for attachment to a second vertebral body;
 a connecting plate adapted to connect the first base plate to the second base plate, the connecting plate comprising a slot though which the connecting plate is connected to the first base plate, wherein the slot has a beveled edge of a first slope.

2. The modular anterior cervical plate assembly of claim 1, further comprising a fastener comprising a surface having a second slope, the second slope being different than the first slope, the fastener being configured to fit into the fastener hole and into the slot such that the surface of the fastener contacts the beveled edge of the slot.

3. The modular anterior cervical plate assembly of claim 2, wherein the fastener is a threaded lock screw.

4. A modular anterior cervical plate assembly comprising:
 a first base plate comprising means for attachment to a first vertebral body and a connecting plate fastener hole;
 a second base plate comprising means for attachment to a second vertebral body;
 a connecting plate adapted to connect the first base plate to the second base plate, the connecting plate comprising a slot though which the connecting plate is connected to the first base plate, wherein at least one of said first and said second base plates further includes a retractor blade knob having a slot for receiving a retractor blade.

5. The modular anterior cervical plate assembly of claim 4, wherein the retractor blade knob has an open end for inserting the retractor blade into the slot.

6. A modular anterior cervical plate assembly comprising:
 a first base plate and second base plate, each base plate having means for attachment to a corresponding vertebral body;
 a connecting plate comprising a slot having a beveled edge of a first slope; and
 a fastener comprising a surface having a second slope, the second slope being different than the first slope, the fastener being configured to fit into the slot such that the surface contacts the beveled edge, and being configured to movably secure said connecting plate to at least one of said first base plate and said second base plate when in the slot.

7. The modular anterior cervical plate assembly of claim 6, wherein at least one of said first and said second base plates further includes a retractor blade knob having a slot for receiving a retractor blade.

8. The modular anterior cervical plate assembly of claim 7, wherein the retractor blade knob has an open end for inserting the retractor blade into the retractor blade knob slot.

9. The modular anterior cervical plate assembly of claim 6, wherein the fastener is a threaded lock screw.

10. The modular anterior cervical plate assembly of claim 6, wherein the fastener is adapted to secure the connecting plate to the first base plate by contacting the edge of the slot by a first surface area amount, and wherein the modular assembly further comprises a second fastener adapted to fit into the slot and to contact the edge of the slot by a second surface area amount that is different from the first surface area amount.

11. The modular anterior cervical plate assembly of claim 10, wherein at least one of first fastener and the second fastener is a threaded lock screw.

12. A modular anterior cervical plate assembly comprising:
   at least two base plates, each base plate having means for attachment to a vertebral body, and
   a connecting plate, said connecting plate having means to movably secure said connecting plate to said base plates, wherein at least one of said first and said second base plates further includes a retractor blade knob having a slot for receiving a retractor blade.

13. The modular anterior cervical plate assembly of claim 1, wherein the retractor blade knob has an open end configured to allow insertion of the retractor blade into the slot.

14. A modular anterior cervical plate assembly comprising:
   a first base plate for engaging a first vertebral body, wherein the first base plate includes a first bone screw hole;
   a second base plate for engaging a second vertebral body, wherein the second base plate includes a second bone screw hole; and
   a connecting plate adapted to connect the first base plate to the second base plate, wherein the connecting plate includes a first slot adapted to movably secure the first base plate to the connecting plate, wherein the first base plate includes a first raised central portion including a first screw hole and wherein the first raised central portion is configured to be inserted in the first slot.

15. The modular anterior cervical plate assembly of claim 14, further comprising a first lock screw adapted to be inserted into the first screw hole.

16. The modular anterior cervical plate assembly of claim 15, wherein the first lock screw has a screw head that is adapted to be spaced from the connecting plate when the first lock screw is inserted into the first screw hole.

17. The modular anterior cervical plate assembly of claim 15, wherein the first lock screw has a screw head and a threaded portion having a first length and the first screw hole has a second length that is less than the first length, so that when the first lock screw is inserted into the first screw hole, the screw head is spaced from the connecting plate.

18. The modular anterior cervical plate assembly of claim 14, wherein the connecting plate includes a second slot adapted to movably secure the second base plate to the connecting plate.

19. The modular anterior cervical plate assembly of claim 18, wherein the second base plate includes a second raised central portion including a second screw hole and wherein the second raised central portion is configured be inserted in the second slot.

20. The modular anterior cervical plate assembly of claim 19, further comprising a second lock screw adapted to be inserted into the second screw hole.

21. The modular anterior cervical plate assembly of claim 20, wherein the second lock screw has a screw head that is adapted to be spaced from the connector plate when the second lock screw is inserted into the second threaded lock screw hole.

22. The modular anterior cervical plate assembly of claim 20, wherein the second lock screw has a screw head and a threaded portion having a first length and the second screw hole has a second length that is less than the first length, so that when the second lock screw is inserted into the second screw hole, the screw head is spaced from the connecting plate.

23. The modular anterior cervical plate assembly of claim 14, further comprising a first lock screw adapted to secure the connecting plate to the first base plate by contacting an edge of the first slot by a first surface area amount and a second lock screw adapted to secure the connecting plate to the first base plate by contacting the edge of the slot by a second surface area amount different from the first surface area amount.

24. A modular anterior cervical plate assembly comprising:
   A) at least two base plates, each base plate comprising
      i) a raised central portion, with a hole
      ii) screw holes for receiving bone screws to attach each said base plate to a corresponding vertebral body, and
      iii) at least one retractor knob configured to receive at least one retractor blade, and
   B) a connecting plate defining slots for accommodating a corresponding one of said base plate raised central portions, and
   C) a connecting screw for movably attaching said connecting plate to one of said base plates.

25. The modular anterior cervical plate assembly of claim 24, wherein the connecting screw comprises a lock screw.

26. The modular anterior cervical plate assembly of claim 25, wherein the lock screw is adapted to be inserted into the hole of the raised central portion of one of the base plates.

27. The modular anterior cervical plate assembly of claim 26, wherein the lock screw has a threaded portion having a length that is greater than the length of the hole, to produce a gap between a head of the lock screw and the connecting plate when the raised central portion of said one of said base plates is inserted in one of said slots of the connecting plate and the lock screw is inserted in the hole.

28. The modular anterior cervical plate assembly of claim 24, wherein the retractor knob includes a slot configured to receive the retractor blade.

29. The modular anterior cervical plate assembly of claim 28, wherein the knob includes an open end for inserting the retractor blade in the slot and a closed end for retaining the retractor blade in the slot.

30. The modular anterior cervical plate assembly of claim 24, wherein the retractor knob is configured to receive a distraction-compression tool.

31. A modular anterior cervical plate assembly comprising:
   a first base plate including a first bone fastener hole adapted to receive a first bone fastener for attaching the first base plate to a first vertebral body;
   a second base plate including a second bone fastener hole adapted to receive a second bone fastener for attaching the second base plate to a second vertebral body;
   a connecting plate adapted to connect the first base plate to the second base plate, the connecting plate comprising a first slot having a beveled edge of a first slope; and
   a first fastener comprising a surface having a second slope, the second slope being different than the first slope, the first fastener being configured to fit into the first slot such that the surface contacts the beveled edge, and the first fastener being configured to movably secure said connecting plate to said first base plate when the first fastener is in the first slot.

32. The modular anterior cervical plate assembly of claim 31, wherein the first base plate includes a first raised central portion including a first fastener hole for receiving the first fastener and wherein the first raised central portion is configured to be inserted into the first slot.

33. The modular anterior cervical plate assembly of claim 31, wherein the first fastener is a threaded lock screw.

34. The modular anterior cervical plate assembly of claim 31, wherein the connecting plate includes a second slot adapted to permit the second base plate to be movably secured to the connecting plate.

35. The modular anterior cervical plate assembly of claim 34, wherein the second base plate includes a second raised central portion including a second fastener hole for receiving a second fastener and wherein the second raised central portion is configured to be inserted into the second slot.

36. The modular anterior cervical plate assembly of claim 35, further comprising a second fastener configured to fit into the second slot, and the second fastener being configured to movably secure said connecting plate to said second base plate when the second fastener is in the second slot.

37. The modular anterior cervical plate assembly of claim 36, wherein the second fastener is a threaded lock screw.

38. The modular anterior cervical plate assembly of claim 31, wherein the first fastener is adapted to secure the connecting plate to the first base plate by contacting the edge of the first slot by a first surface area amount, and wherein the modular assembly further comprises a second fastener configured to fit into the first slot configured to movably secure the connecting plate to the first base plate by contacting the edge of the first slot by a second surface area amount that is different from the first surface area amount.

39. The modular anterior cervical plate assembly of claim 38, wherein the first fastener and the second fastener both are threaded lock screws.

40. A modular anterior cervical plate assembly comprising:
a first base plate comprising a first bone fastener hole adapted to receive a first bone fastener adapted to attach the first base plate to a first vertebral body, and a first connecting plate fastener hole;
a second base plate comprising a second bone fastener hole adapted to receive a second bone fastener adapted to attach the second base plate to a second vertebral body;
a connecting plate adapted to connect the first base plate to the second base plate, the connecting plate comprising a first slot;
a first fastener configured to fit into the first connecting plate fastener hole adapted to secure the connecting plate to the first base plate; and
wherein the first fastener has a head, the first fastener being configured such that the head is spaced apart from the connecting plate and the first base plate when the first fastener is inserted into the first connecting plate fastener hole.

41. The modular anterior cervical plate assembly of claim 40, wherein the first base plate includes a first raised central portion including the first connecting plate fastener hole adapted to receive the first fastener and wherein the first raised central portion is configured to be inserted into the first slot.

42. The modular anterior cervical plate assembly of claim 40, wherein the first fastener has a threaded portion having a first length and the first connecting plate fastener hole has a second length that is less than the first length, so that when the first fastener is inserted into the first connecting plate fastener hole, the head is spaced from the connecting plate.

43. The modular anterior cervical plate assembly of claim 40, wherein the first fastener is a threaded lock screw.

44. The modular anterior cervical plate assembly of claim 40, wherein the connecting plate includes a second slot adapted to permit the second base plate to be movably secured to the connecting plate.

45. The modular anterior cervical plate assembly of claim 44, wherein the second base plate includes a second raised central portion including a second connecting plate fastener hole adapted to receive a second fastener and wherein the second base plate comprises a second raised central portion is configured be inserted in the second slot.

46. The modular anterior cervical plate assembly of claim 45, further comprising the second fastener configured to fit into the second connecting plate fastener hole adapted to movably secure the connecting plate to the second base plate.

* * * * *